(12) United States Patent
Cho et al.

(10) Patent No.: US 9,309,519 B2
(45) Date of Patent: Apr. 12, 2016

(54) METHOD FOR SELECTING A HIGH EXPRESSION RECOMBINANT CELL LINE

(75) Inventors: MyungSam Cho, Incheon (KR); Min Seok Chang, Incheon (KR); Jong-Mook Kim, Incheon (KR); HyunJoo Lee, Incheon (KR); Yoo Cheol Song, Incheon (KR); ManSu Kim, Incheon (KR)

(73) Assignee: CELLTRION INC. (KR)

( * ) Notice: Subject to any disclaimer, the term of this patent is extended or adjusted under 35 U.S.C. 154(b) by 135 days.

(21) Appl. No.: 13/255,004

(22) PCT Filed: Mar. 30, 2010

(86) PCT No.: PCT/KR2010/001912
§ 371 (c)(1),
(2), (4) Date: Sep. 6, 2011

(87) PCT Pub. No.: WO2010/114270
PCT Pub. Date: Oct. 7, 2010

(65) Prior Publication Data
US 2012/0009682 A1    Jan. 12, 2012

(30) Foreign Application Priority Data

Mar. 31, 2009  (KR) .................. 10-2009-0027871

(51) Int. Cl.
| | | |
|---|---|---|
| C12N 15/65 | (2006.01) | |
| C12N 15/67 | (2006.01) | |
| C12N 15/10 | (2006.01) | |
| C12N 15/85 | (2006.01) | |
| C12P 21/02 | (2006.01) | |
| C12N 15/69 | (2006.01) | |

(52) U.S. Cl.
CPC ............ *C12N 15/65* (2013.01); *C12N 15/1086* (2013.01); *C12N 15/69* (2013.01); *C12N 15/85* (2013.01); *C12P 21/02* (2013.01); *C12N 2800/24* (2013.01); *C12N 2830/46* (2013.01); *C12N 2830/50* (2013.01)

(58) Field of Classification Search
CPC .... C12N 2830/42; C12N 15/63; C12N 15/67; C12N 15/69; C12N 2510/00; C12N 2510/02; C12N 9/003; C12N 15/65; C12Y 105/01003
See application file for complete search history.

(56) References Cited

U.S. PATENT DOCUMENTS

| | | |
|---|---|---|
| 5,733,779 A | 3/1998 | Reff |
| 6,524,818 B1 | 2/2003 | Harrington et al. |
| 6,632,637 B1 | 10/2003 | McGrew |
| 2004/0063186 A1 | 4/2004 | McGrew |

FOREIGN PATENT DOCUMENTS

| | | |
|---|---|---|
| JP | 2003511079 | 3/2003 |
| WO | 2010/114270 A2 | 10/2010 |
| WO | 2010/114270 A3 | 10/2010 |

OTHER PUBLICATIONS

Ishida et al, Nucleic Acids Research, 1999, 27: pe35i-e35vii.*
Ishida et al, Nucleic Acids Research, 1999, 27:e35i-e35viii.*
Abrams et al, J Biol Chem, 1989, 264:14016-14021.*
Lucas et al, Nucleic Acids Research, 1996, 24:1774-1779.*
Wickens et al, Current Opinion in Genetics and Development, 1997, 7:220-232.*
Blokland et al, Journal of Biotechnology, 2007, 128:237-245.*
Niwa et al, Gene, 1991, 108:193-200.*
Sautter and Enenkel, Biotechnology and Bioengineering, 2005, 89:530-538.*
Ng et al, Metabolic Engineering, 2007, 9:304-316.*
Goh et al, BMC Biotechnol, 2008, 8:61.*
Sugimoto et al, Journal of Cerebral Blood Flow and Metabolism, 1997, 17:44-49.*
Zeevi et al, Mol Cell Biol,1982, 2:517-525.*
International Search Report with English Translation for Application No. PCT/KR2010/001912 dated Dec. 15, 2010.
Lucas, et al., High-level production of recombinant proteins in CHO cells using a dicistronic DHFR intron expression vector, Nucleic Acids Research, 1996, vol. 24, No. 9 pp. 1774-1779.
Peakman, et al., Comparison of expression of a humanized monoclonal antibody in mouse NSO myeloma cells and Chinese Hamster Ovary cells, Hum. Antibod. Hybridomas, 1994, vol. 5, 1 and 2 pp. 65-74.

(Continued)

*Primary Examiner* — Anoop Singh
*Assistant Examiner* — David A Montanari
(74) *Attorney, Agent, or Firm* — Cantor Colburn LLP

(57) ABSTRACT

The present invention relates to a method of selecting high producer clones by using an expression vector, the expression vector comprising: (i) a gene expression cassette comprising a selectable marker gene to which polyA has been inoperably linked; and (ii) a gene expression cassette which encodes a recombinant protein of interest and to which polyA has been operably linked. According to the invention, high producer clones can be selected from cell populations at least 10 times fewer than in the existing methods of selecting cell lines. Particularly, high producer clones can be selected using a low concentration of MTX compared to a conventional stepwise gene amplification strategy which comprises carrying out multiple amplification steps while increasing the concentration of MTX. Accordingly, the development period of cell lines can be shortened and the labor and cost required for selection of high-productivity cell clones can be reduced, whereby more efficient production of proteins is possible even when general selectable marker genes other than MTX are used.

2 Claims, 13 Drawing Sheets

(56) References Cited

OTHER PUBLICATIONS

Ogata, et al., High-level expression of recombinant human soluble thrombomodulin in serum-free medium by CHO-K1 cells, Appl Microbiol Biotechnol (1993) 38:520-525.

Kratje, et al., Cultivation of Recombinant Baby Hamster Kidney Cells in a Fluidized Bed Bioreactor System with Porous Borosilicate Glass, Biotechnol. Prog. 1994, 10, 410-420.

Niwa, et al., Efficient selection for high-expression transfectants with a novel eukaryotic vector, Gene, 108 (1991) 193-200.

Sautter, et al., Selection of High-Producing CHO Cells Using NPT Selection Marker With Reduced Enzyme Activity, Biotechnology and Bioengineering, vol. 89, No. 5, Mar. 5, 2005 pp. 530-538.

van Blokland, et al., A novel, high stringency selection system allows screening of few clones for high protein expression, Journal of Biotechnology 128 (2007) 237-245.

Ishida, et al., RET: a poly A-trap retrovirus vector for reversible disruption and expression monitoring of genes in living cells, Nucleic Acids Research, 1999, vol. 27, No. 24 pp. 1-8.

Salminen, et al., Efficient Poly a Trap Approach Allows the Capture of Genes Specifically Active in Differentiated Embryonic Stem Cells and in Mouse Embryos, Developmental Dynamics 212:326-333 (1998).

Matsuda, et al., Expression profiling with arrays of randomly disrupted genes in mouse embryonic stem cells leads to in vivo functional analysis, 4170-4174 PNAS Mar. 23, 2004 vol. 101 No. 12.

Friedel, et al., Gene targeting using a promoterless gene trap vector ("targeted trapping") is an efficient method to mutate a large fraction of genes, 13188-13193 PNAS Sep. 13, 2005 vol. 102 No. 37.

Hardouin, et al., Gene-Trap-Based Target Site for Cre-Mediated Transgenic Insertion, genesis 26:245-252 (2000).

Written Opinion of the International Searching Authority with English Translation for International Application No. PCT/KR2010/001912 dated Dec. 15, 2010.

D.S. Pfarr et al., Differential Effects of Polyadenylation Regions on Gene Expression in Mammalian Cells, DNA, vol. 5, No. 2, 1986, pp. 115-122.

E.R. Gimmi et al., Deletions in the SV40 late polyadenylation region downstream of the AATAAA mediate similar effects on expression in various mammalian cell lines, Nucleic Acids Research, vol.16, No. 18, 1988, pp. 8977-8997.

Japanese Office Action for Japanese Patent Application No. 2012-503316 dated Jul. 4, 2013.

Chinese Office Action for Chinese Patent Application No. 201080013851.X dated Oct. 29, 2013 with English Translation.

Examination Report for European Patent Application No. 10758995.4 dated Oct. 17, 2013.

SB Primrose and RM Twyman, "Principles of Gene Manipulation and Genomics", Jan. 1, 2007, Blackwell Publishing, p. 232.

Goldsmith ME, et al., "Modulation of a human dihydrofolate reductase minigene following release from amino acid deprivation involves both 5' and 3' nucleotide sequences", Mol Phamacol., vol. 33(4), 1988, pp. 378-383 (abstract only).

Indian Office action for Indian Patent Application No. 6741/CHENP/2011 dated Aug. 22, 2014.

* cited by examiner

METHOD FOR SELECTING A HIGH EXPRESSION RECOMBINANT CELL LINE

TECHNICAL FIELD

The present invention relates to a method of selecting cell lines for high expression of a protein of interest (hereinafter referred to as "high producer clone"), and more particularly to a method of selecting high producer clones by using an expression vector, the expression vector comprising: (i) a gene expression cassette comprising a selectable marker gene to which a polyadenylation signal (polyA) has been inoperably linked; and (ii) a gene expression cassette which encodes a recombinant protein of interest and to which polyA has been operably linked, and to the expression vector.

BACKGROUND ART

In the biological or medical field, a protein of interest to be produced is obtained by inserting the gene of the protein into an expression vector, transfecting the expression vector into a cell line producing the protein, culturing the resulting cell line in a large amount, and isolating and purifying the cultured cell line using a suitable method.

Examples of methods which are industrially used for this purpose include methods that use CHO (Chinese hamster ovary) dhfr (dihydrofolate reductase) (−), CHO K1, BHK (Baby Hamster Kidney), NS0, SP2/0 and human cell lines (Ogata, et al., Appl. Microbiol. Biotechnol., 1993, 38(4), 520-525; Kratje, et al., Biotechnol. Prog., 1994, 10(4), 410-20; Peakman, et al., Hum. Antibodies Hybridomas, 1994, 5(1-2), 65-74).

In order to produce a stable mammalian cell line which expresses a heterologous gene of interest, the heterologous gene is generally introduced into the desired cell line together with a selectable marker gene (e.g. neomycin phosphotransferase) by transfection. The heterologous gene and the selectable marker gene can be expressed either together by a single vector or by separate vectors which are co-transfected. Two to three days after transfection, the cells are transferred into a medium containing a selective agent, for example, G418 in case of using neomycin phosphotransferase-gene as a selectable marker gene, and cultured for several weeks under these selective conditions. The emergent resistance cells can then be isolated and investigated for expression of the desired gene product. As a result of the random and non-directed integration into the host cell genome, populations of cells are obtained which have completely different rates of expression of the heterologous gene. These may also include non-expressing cells in which the selectable marker is expressed but not the gene of interest. In order to identify cell clones which have a very high expression of the heterologous gene of interest, it is therefore necessary to examine and test a large number of clones, which is time-consuming, labor-intensive and expensive.

Gene amplification is a common technique in animal cell cultures for use in the production of recombinant proteins. The gene amplification significantly improves the relatively low productivity of numerous mammalian cell lines. One amplification technique widely used in the art is a dihydrofolate reductase (dhfr)-based gene amplification system which is very often used in dhfr-deficient CHO cells.

The reasons why the dhfr-deficient CHO cell line is industrially preferred are as follows: (1) posttranslational modification of protein (glycosylation or phosphorylation) is more similar to that of human cells than other cells; (2) not only adhesion culture, but also suspension culture are possible; (3) these cells can be cultured at relatively high concentrations in a serum-free medium compared to other cells; (4) the productivity of the protein of interest, which is significantly low compared to that of microorganisms, can be increased using a dhfr/MTX (methotrexate) gene amplification system; and (5) these cells have been proven safe and can thus be easily approved by relevant authorities such as the FDA. For the above-described reasons, the dhfr-deficient CHO cell line has been widely used for industrial purposes to construct a recombinant cell line producing a protein of interest.

However, even when the conventional dhfr/MTX gene amplification system is used that can significantly increase the production of the protein of interest via introduction of the gene encoding the protein of interest into dhfr-deficient CHO cells and then treatment of the cells with stepwise increasing concentrations of MTX, selecting cell populations having high productivity is labor-intensive, time and cost-consuming, because a process of treating the cells with increasing concentrations of MTX for a long time is required and the number of cell populations to be screened in this process is 500-4,000 or more. Accordingly, efforts to simplify this selection have been attempted in various ways.

For example, researchers in the art have made efforts to simplify the selection step using 1) a method of reducing the expression of a selectable marker gene by modifying the vicinity of the start codon (Reff, U.S. Pat. No. 5,733,779, 1998); 2) a method of impairing the function of a selectable marker gene by mutating the gene (Nivea et al., Gene 108, 193-200, 1991; Sauter and Enenkel, Biotechnol. Bioeng. 89, 530-538, 2005); 3) a method of modifying the start codon itself and linking the modified start codon with a gene to be expressed, thereby increasing the expression level of the gene (van Blokland et al., J of Biotechnology 128, 237-245, 2007); and 4) a method of linking a selectable marker gene to an intron and expressing the gene (Lucas et al., Nucleic Acids Res. 24, 1774-1779, 1996).

DISCLOSURE

Technical Problem

It is, therefore, an object of the present invention to provide a method of selecting high producer clones by using an expression vector comprising a selectable marker gene to which a polyadenylation signal (polyA) has been inoperably linked.

Another object of the present invention is to provide an expression vector which is used in said selection method.

Still another object of the present invention is to provide a eukaryotic host cell line transfected with said expression vector.

Technical Solution

To achieve the above objects, the present invention provides a method of selecting high producer clones by using an expression vector, the expression vector comprising: (i) a gene expression cassette comprising a selectable marker gene to which a polyadenylation signal (polyA) has been inoperably linked; and (ii) a gene expression cassette which encodes a recombinant protein of interest and to which polyA has been operably linked.

The present invention also provides an expression vector comprising: (i) a gene expression cassette comprising a selectable marker gene to which polyA has been inoperably linked; and (ii) a gene expression cassette which encodes a recombinant protein of interest and to which polyA has been operably linked.

The present invention also provides a eukaryotic host cell line transfected with said expression vector.

Hereinafter, the definition of terms that are used in the present invention will be described.

As used herein, the term "selectable marker gene" refers to a marker gene that has been linked with the gene of a protein of interest and inserted into an expression vector, thereby allowing identification of the cells in which the gene of interest is normally expressed. When an inhibitor of a protein which is encoded by the selectable marker gene is added to a medium, the copy number of the selectable marker gene or the copy number of the gene of the protein of interest linked to the selectable marker gene can be increased. Examples of the selectable marker include dhfr gene, glutamine synthetase gene, neomycine phosphotransferase gene, hygromycin B phosphotransferase gene, puromycin-N-acetyltransferase (pac) gene, and *Streptoalloteichus hindustanus* (Sh) ble gene.

The term "polyA" as used herein, refers to a signal sequence which causes cleavage at a specific site at the 3' end of the eukaryotic mRNA and post-transcriptional incorporation of a sequence of about 100-200 adenine nucleotides (polyA tail) at the cleaved 3' end. The polyA refers to the consensus sequence AATAAA about 10-30 nucleotides upstream of the cleavage site and a sequence located downstream. Various polyAs are known such as tk polyA, SV40 late and early polyA or BGH polyA.

The term "operably linked" as used herein, means that one nucleic acid fragment links to a second nucleic acid fragment so that its function or expression is influenced by the second nucleic acid fragment. Also, the term "operably linked" is used to describe a linkage between a gene sequence and a promoter or other regulatory or processing sequence such that the transcription of the gene sequence is directed by an operably linked promoter sequence, the translation of the gene sequence is directed by an operably linked translational regulatory sequence, or the post-translational processing of the gene sequence is directed by an operably linked processing sequence. The term "inoperably linked" has a meaning contrary to the term "operably linked" and is generally intended to include the linkage that has become inoperable due to artificial manipulation by methods such as cleavages, deletions, point mutations and amino acid replacements which are known to those skilled in the art.

Hereinafter, the present invention will be described in detail.

The inventors have conducted studies on a novel method of selecting high producer clones and, as a result, have found that polyA greatly influences the transcription and stability of mRNA and that, when the length of polyA becomes somewhat short with the passage of time, mRNA starts to be degraded, and for this reason, if the polyA does not normally operate, the half-life of the mRNA is very short compared to that of normal mRNA. Based on this finding, the inventors have conducted studies to develop a novel selection method while paying attention to polyA.

For example, when polyA linked to a selectable marker gene in an expression vector is made inoperable and is then transfected into host cells which are then cultured under selective conditions in which an inhibitor of the protein that is encoded by the selectable marker gene is present, the selectable marker gene on which polyA does not normally operate cannot stably produce mRNA, and thus most cells will be killed under the selective conditions, and only cells transfected with a large number of copies of vectors can survive.

Because the expression vector used for the transfection includes the selectable marker gene together with a gene encoding the recombinant protein of interest, the gene encoding the recombinant protein of interest is present in a large copy numbers in proportion to the copy number of the selectable marker gene.

In order to demonstrate the use of operability of the polyA linked to the selectable marker gene as a novel method for selecting high producer clones, in the present invention, the polyA linked to the 3' end of the selectable marker gene dhfr on a pCT107 vector (see FIG. 1) was cleaved with a suitable restriction enzyme to make the polyA inoperable. Then, the resulting expression vector was transfected into a CHO DG44 cell line (test group), and a process of selecting high producer clones from the cell line was compared with that from a CHO DG44 cell line (control group) transfected with a pCT107 vector untreated with a restriction enzyme. The result showed that in the test group, the number of wells per plate in which cells grew, was about 7.6 times smaller than that in the control group, and the ratio of growing cells was (1/26264):(1/814815), suggesting that the ratio of growing cells in the test group was 31 times lower than that in the control group (see Table 2).

Then, in order to compare the productivities of growing cells between the control group and the test group, six cell lines showing the highest productivity were selected from each group, and their productivities were investigated. It was found that, in the case of the control group, only one p-clone among the six p-clones showed a productivity of about 100 µg/µl/3 days, whereas in the case of the test group, four p-clones among the six p-clones showed a productivity of about 100 µg/µl/3 days (see FIG. 6).

Also, in order to confirm whether the above-described selection method of the present invention is also applied to other systems than the system that uses the dhfr selectable marker in CHO DG44 cells, an experiment was carried out using a system with a pac selectable marker in CHO K1 cells. For this purpose, a dhfr transcription unit (promoter-dhfr-polyA) on a pCT112 vector (see FIGS. 7 and 8) was removed, and a SV40 promoter and a pac gene were inserted into the vector, thereby constructing a test vector (pCT130 vector; see FIG. 7). Also, SV40 promoter, pac gene and polyA (pac transcription unit) were inserted into the vector to construct a control vector (pCT129 vector; see FIG. 8). Then, each of the constructed vectors was transfected into CHO K1 cells, and control cell lines and test cell lines were selected, followed by investigation of the productivities of the selected cells lines. As can be seen in FIGS. 9 to 13, the productivity of clones derived from the test group (pCT130 vector) was higher than that of clones derived from the control group (pCT129 vector). It was found that in shake-flask batch culture showing more substantial productivity than that obtained in the well-plate based selection step, the productivity of single cell-derived clones from the test group (67-72 µg/ml was much higher than the productivity of single cell-derived clones from the control group (2-10 µg/ml.

As a result, the inventors have found that the selection method according to an embodiment of the present invention is useful in reducing the cost and time for selecting high producer clones via use of various selectable markers, thereby completing the present invention.

In one aspect, the present invention provides a method of selecting high producer clones by using an expression vector, the expression vector comprising: (i) a gene expression cassette comprising a selectable marker gene to which polyA has been inoperably linked; and (ii) a gene expression cassette which encodes a recombinant protein of interest and to which polyA has been operably linked.

In an embodiment of the present invention, the expression marker may comprise, in place of the gene expression cassette (i) comprising the selectable marker gene to which the polyA has been inoperably linked, a gene expression cassette comprising a selectable marker gene from which polyA has been removed.

In another aspect, the present invention also provides a method of selecting high producer clones, the method comprising cleaving an expression vector with a suitable restriction enzyme, the expression vector comprising (i) a gene expression cassette containing a selectable marker gene to which polyA has been operably linked and (ii) a gene expression cassette which encodes a recombinant protein of interest and to which polyA has been operably linked, thereby linearizing the expression vector such that the polyA of the gene expression cassette (i) does not operate.

In an embodiment of the present invention, examples of the selectable marker gene include, but are not limited to, dhfr gene, glutamine synthetase gene, neomycine phosphotransferase gene, hygromycin B phosphotransferase gene, puromycin-N-acetyltransferase (pac) gene, and *Streptoalloteichus hindustanus* (Sh) ble gene. In addition to these marker genes, any selectable marker gene that is known to a person skilled in the art may be used in the present invention.

In an embodiment of the present invention, the recombinant protein of interest is preferably, but not limited to, a monoclonal antibody.

In an embodiment of the present invention, examples of the host cells include, but are not limited to, eukaryotic host cells, preferably human host cells, including CHO cells, hybridoma cells or F2N cells. In addition to these cells, any cell line that is known to a person skilled in the art as a recombinant protein-producing cell line may be used in the present invention.

In a further aspect, the present invention also provides an expression vector comprising: (i) a gene expression cassette comprising a selectable marker gene to which polyA has been inoperably linked; and (ii) a gene expression cassette which encodes a recombinant protein of interest and to which polyA has been operably linked.

In an embodiment of the present invention, the expression vector may comprise, in place of the gene expression cassette (i) comprising the selectable marker gene to which the polyA has been inoperably linked, a gene expression cassette comprising a selectable marker gene from which polyA has been removed.

In an embodiment of the present invention, the expression vector may comprise, in place of the gene expression cassette (ii) which encodes the recombinant protein of interest and to which the polyA has been operably linked, a multiple cloning site for introduction of a gene encoding the recombinant protein of interest.

In an embodiment of the present invention, the selectable marker gene is an amplifiable selectable marker gene, preferably, but not limited to, dhfr gene or glutamine synthetase gene.

In an embodiment of the present invention, the selectable marker gene is, but not limited to, neomycine phosphotransferase gene, hygromycin B phosphotransferase gene, pac gene, or Sh ble gene.

In an embodiment of the present invention, the recombinant protein of interest is preferably, but not limited to, a monoclonal antibody.

In a further aspect, the present invention provides a eukaryotic host cell line transfected with said expression vector.

In an embodiment of the present invention, the host cells are preferably animal cells. In Examples of the present invention, a CHO cell line was used, but the host cell that can be used in the present invention is not limited thereto. Recombinant protein-producing cell lines known to a person skilled in the art, including hybridoma cells or F2N cells, may all be used in the present invention. The transfection is preferably performed using a method known to a person skilled in the art.

Advantageous Effects

According to the present invention, high producer clones can be selected from cell populations at least 10 times fewer than those in existing cell line selection methods. In particular, high producer clones can be selected using low concentrations of MTX compared to a conventional stepwise gene amplification strategy carrying out multiple amplification steps while increasing the concentration of MTX. Accordingly, the development period of cell lines can be shortened and the labor and cost required can be reduced for selection of high producer clones, whereby more efficient production of recombinant proteins is possible.

DESCRIPTION OF DRAWINGS

In FIG. 2, control group (A): a circular pCT107 vector not treated with a restriction enzyme; test group (B): a linear pCT107 vector in which a polyA linked to dhfr gene, has been made inoperable by treatment with Rsr II; test group (C): a linear pCT107 vector in which a polyA linked to the heavy-chain gene, has been made inoperable by treatment with Pme I; and test group (D): a linear pCT107 vector in which a polyA linked to the light-chain gene, has been made inoperable by treatment with Cla I. In the cases in which a sample contained neither heavy chain nor light chain (test group (C) and test group (D)), the titer of IgG was not measured due to the characteristics of ELISA. The experiment was carried out a total of five times, and the error range was expressed as a standard error.

In FIG. 3, uncut: a normal circular pCT107 vector; and RsrII cut: a linear pCT107 vector in which a polyA linked to dhfr gene, has been made inoperable by treatment with Rsr II.

In FIG. 4, uncut: a normal circular pCT107 vector; and RsrII cut: a linear pCT107 vector in which a polyA linked to dhfr gene, has been made inoperable by treatment with Rsr II.

In FIG. 5, uncut: a normal circular pCT107 vector; and RsrII cut: a linear pCT107 vector in which a polyA linked to dhfr gene, has been made inoperable by treatment with Rsr II.

Figure 6:
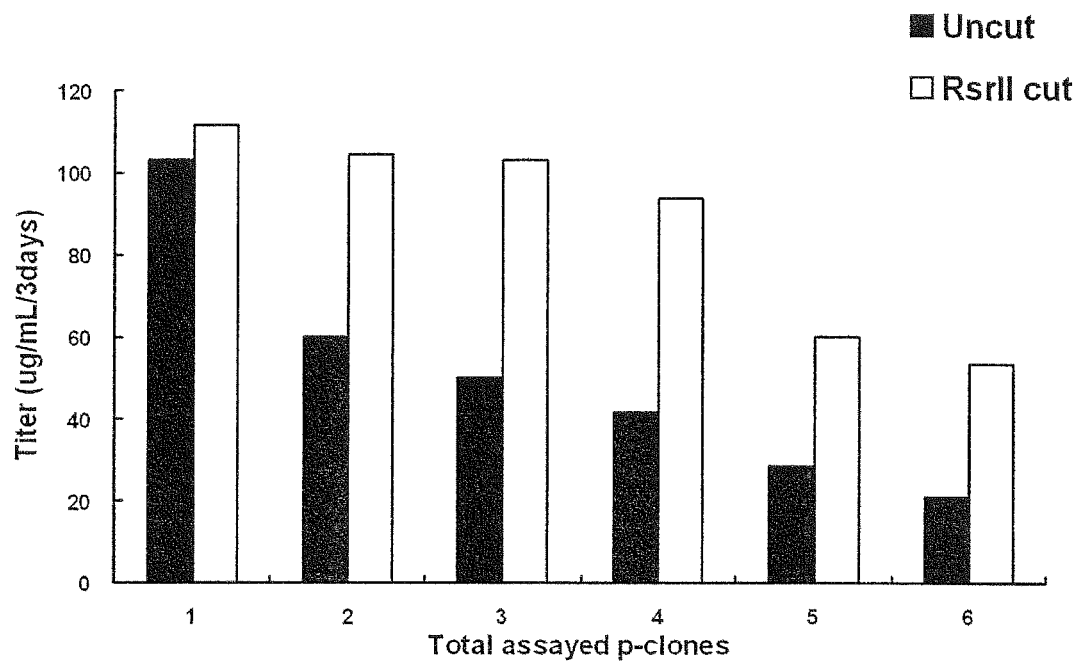

FIG. 6 is a graph showing the results of comparing the productivities of six p-clones from each of a control group and a test group, in shake-flask batch culture conditions, in which the p-clones were those selected for high titers depending on the presence or absence of a polyAfor a control group and a test group. In FIG. 6, uncut: a normal circular pCT107 vector; and RsrII cut: a linear pCT107 vector in which a polyA linked to dhfr gene, has been made inoperable by treatment with Rsr II.

Figure 7:
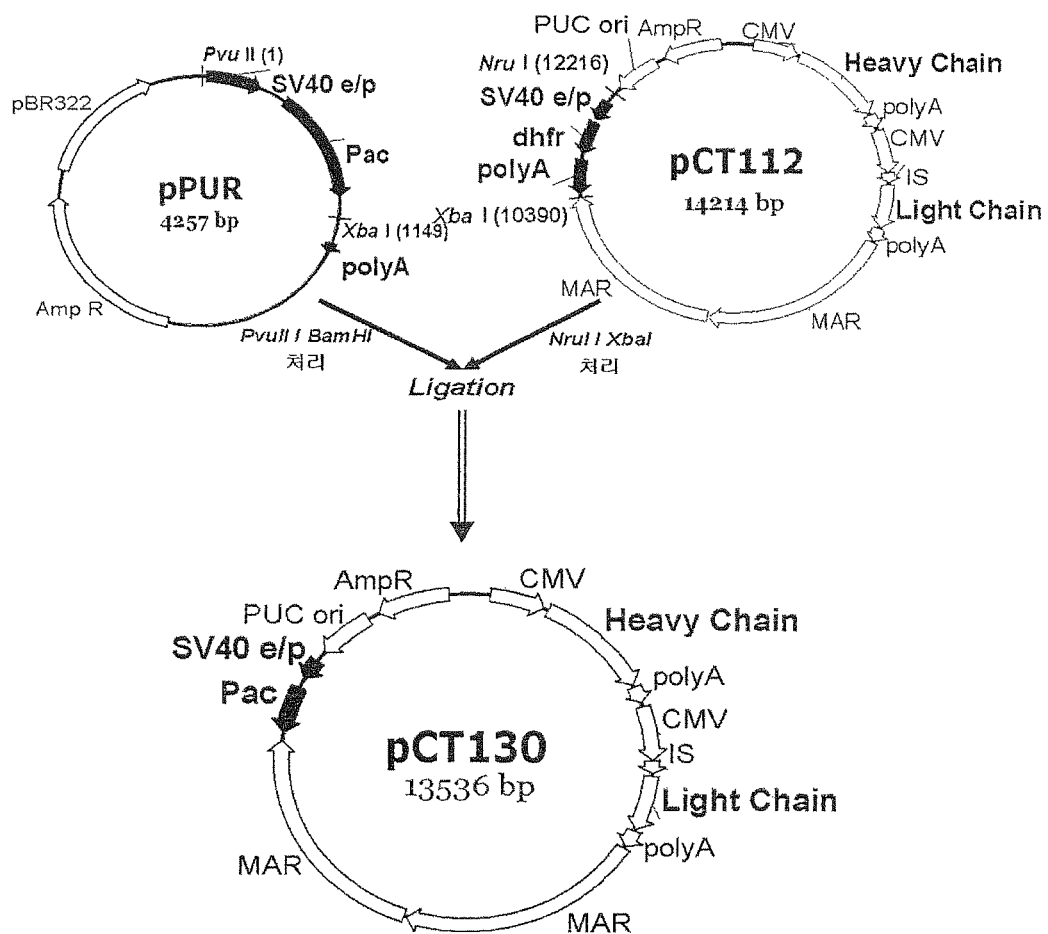

FIG. 7 is a schematic diagram showing a process of cloning a pCT130 expression vector.

Figure 8:
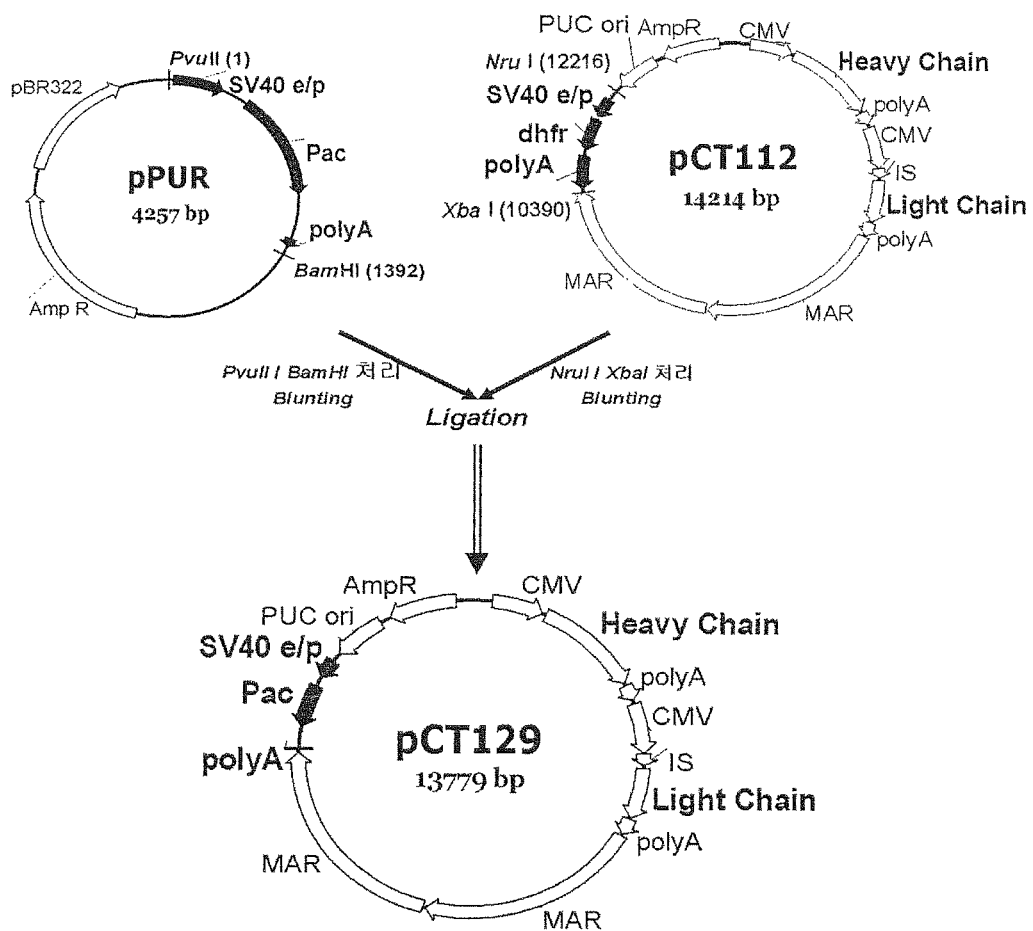

FIG. 8 is a schematic diagram showing a process of cloning a pCT129 expression vector.

Figure 9:
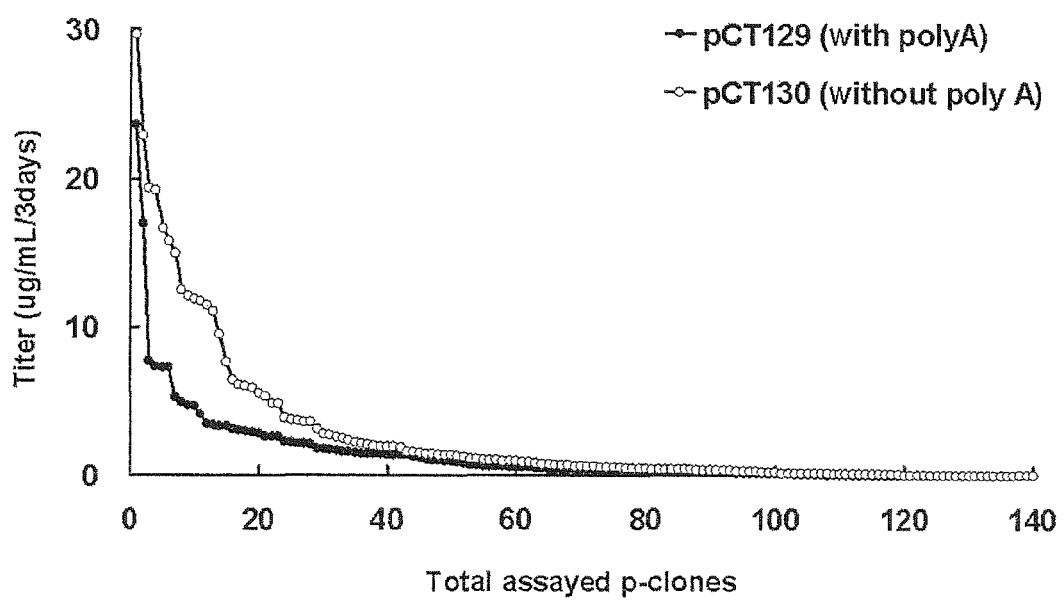

FIG. 9 is a graph showing the results of comparing the productivities of a control group and a test group at the 96-well plate scale. In FIG. 9, pCT129 (with polyA): a control group having polyA activity; and pCT130 (without polyA): a polyA-deleted test group.

Figure 10:
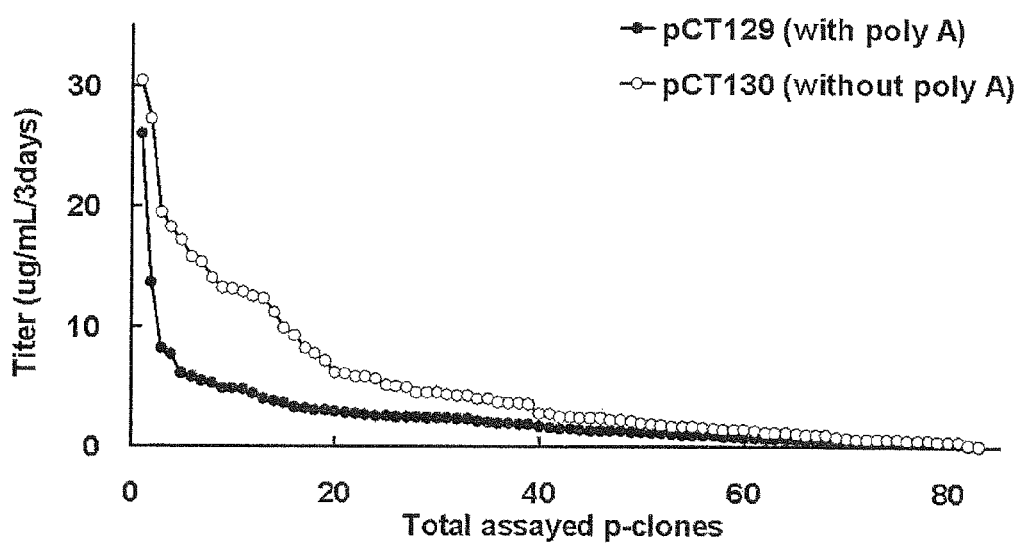

FIG. 10 is a graph showing the results of comparing the productivities of a control group and a test group at the 24-well plate scale. In FIG. 10, pCT129 (with polyA): a control group having polyA activity; and pCT130 (without polyA): a polyA-deleted test group.

Figure 11:
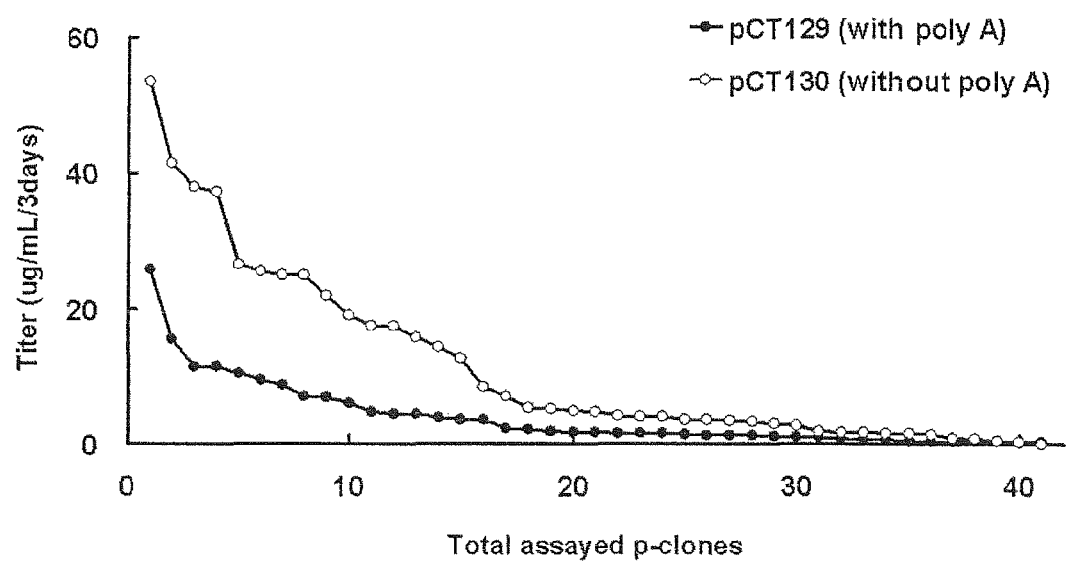

FIG. 11 is a graph showing the results of comparing the productivities of a control group and a test group at the E-well plate scale. In FIG. 11, pCT129 (with polyA): a control group having polyA activity; and pCT130 (without polyA): a polyA-deleted test group.

Figure 12:
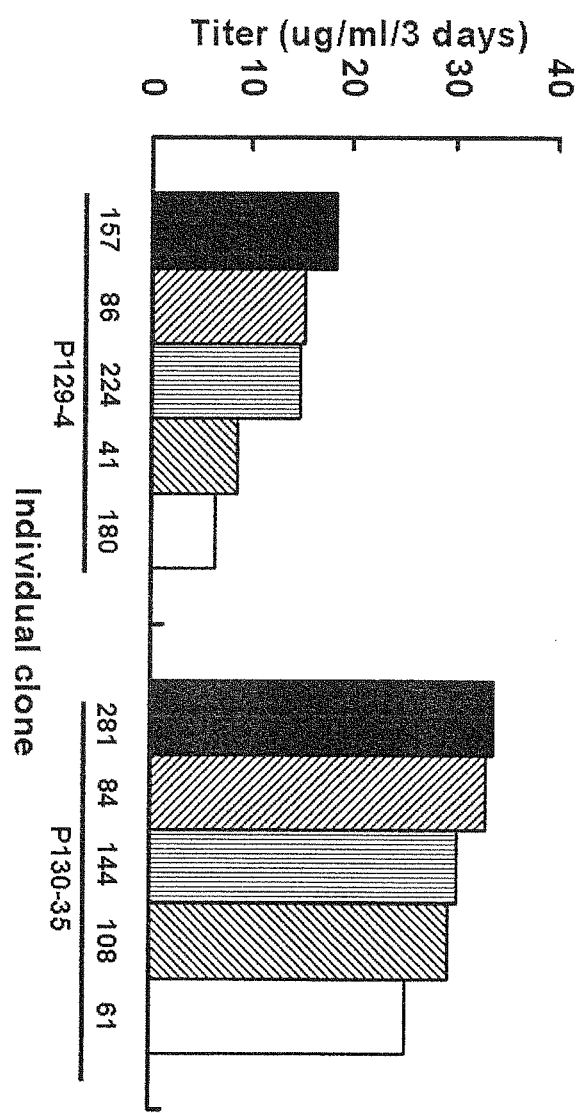

FIG. 12 is a graph showing the results of comparing the productivities of a control group and a test group at the E-well plate scale.

Figure 13:
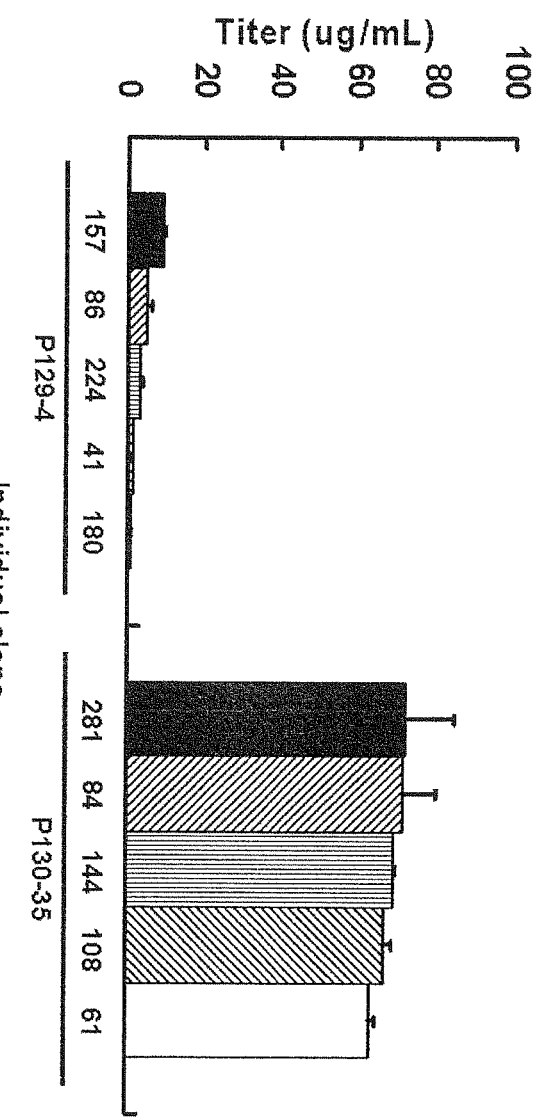

FIG. 13 is a graph showing the results of comparing the productivities of a control group and a test group in batch culture using a shake flask.

BEST MODE

Abbreviations dhfr: dihydrofolate reductase
CHO: Chinese Hamster Ovary
polyA: polyadenylation signal
p-clone: a preliminary clone that is not a single cell-derived clone
MTX: methotrexate
ELISA: Enzyme-Linked Immunosorbent Assay Hereinafter, the present invention will be described in detail with reference to examples. It is to be understood, however, that these examples are for illustrative purposes only and are not to be construed to limit the scope of the present invention.

Example 1

Induction of Inoperable polyA

Figure 1:
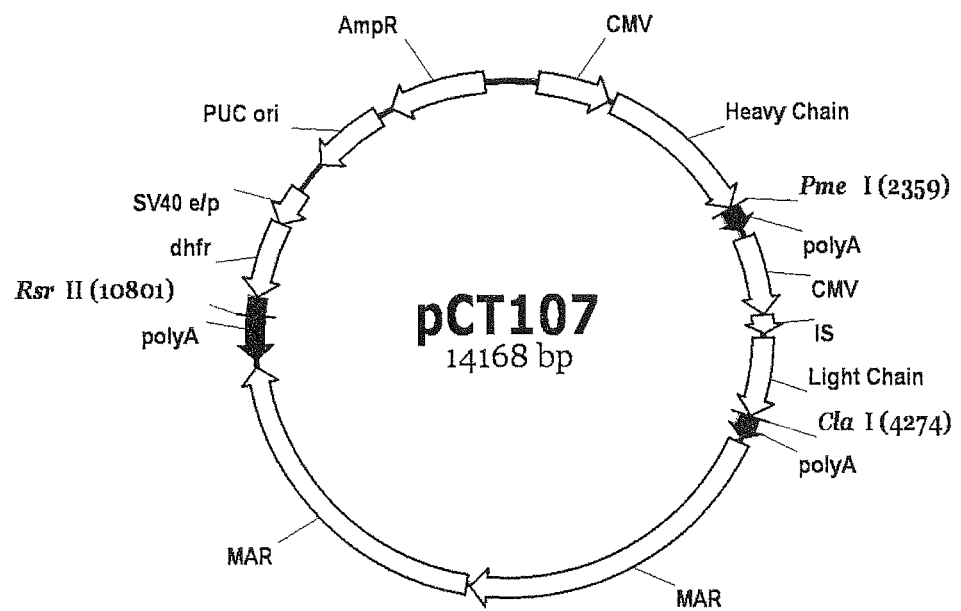
FIG. 1 is a cleavage map of a pCT107 expression vector. The restriction enzymes Pme I, Cla I and Rsr II indicated on the map denote sites at which the pCT107 vector is cleaved such that polyAs linked to the heavy-chain gene, light-chain gene of an antibody and DHFR gene which are encoded by the pCT107 expression vector do not operate.

In a first step for examining the expression level of a gene depending on the presence or absence of a polyA, in order to make inoperable the polyAs operably linked to the 3' end of three transcription units, dhfr gene, a heavy-chain gene and a light-chain gene, in an IgG antibody-expressing pCT107 vector (FIG. 1), the pCT107 vector was cleaved with each of Rsr II, Pme I and Cla I restriction enzymes. The restriction enzymes Rsr II, Pme I and Cla I are enzymes that linearize the IgG antibody-expressing vector by specifically recognizing and cleaving a specific sequence present between the 3' end of each of the dhfr gene, the heavy-chain gene and the light-chain gene and the corresponding polyA.

Treatment with the restriction enzymes was carried out in the following manner. Three tubes were prepared, and (i) 30 µg of a pCT107 vector DNA and 10 U of Rsr II (R0501S, NEB), (ii) 30 µg of a pCT107 vector DNA and 10 U of Pme I (R0560S, NEB) 10 U, and (iii) 30 µg of a pCT107 vector DNA and 10 U of Cla I (R1097S, NEB) were added and mixed in the tubes, respectively, and incubated at 37° C. for 4 hours. Next, 0.1 volume of NaOAC based on the total volume of the sample and 3 volumes of 100% ethanol (EtOH) were to added to the total sample in each tube and vortexed, and then allowed to stand at −70° C. for 30 minutes to precipitate DNA pellets. Then, the content of each tube was centrifuged at 13,000 rpm for 10 minutes to precipitate the DNA pellets on the tube bottom, and ethanol remaining in each tube was removed. Then, the pellets were washed with the same volume of 70% ethanol and centrifuged at 13,000 rpm for 10 minutes, and ethanol remaining in each tube was removed. Then, the DNA pellets were dried in air for 10 minutes. Distilled water was added to the dried pellets and allowed to stand at room temperature for 10 minutes. Then, the DNA pellets were resuspended using a pipette such that they could be completely dissolved in distilled water. The concentration of the DNA was measured using Nanodrop 1000 (Thermo scientific), and then agarose gel electrophoresis was conducted to confirm whether the vector DNA was linearized by the Rsr II, Pme I or Cla I restriction enzyme. The linearization of the expression vectors suggests that the polyAs linked to the three transcription units (heavy-chain gene, light-chain gene and dhfr gene) in the pCT107 vectors all became inoperable.

Example 2

Transfection into CHO Cell Line

The vectors linearized according to Example 1 were transfected into CHO DG44 cells in the same amount. Transfection into the control group and test groups shown in Table 1 below was carried out.

TABLE 1

| Control group (A) | Circular pCT107 vector not treated with restriction enzyme |
|---|---|
| Test group (B) | Linear pCT107 vector in which polyA linked to dhfr, has been made inoperable by treatment with Rsr II. |
| Test group (C) | Linear pCT107 vector in which polyA linked to dhfr, has been made inoperable by treatment with Pme I. |
| Test group (D) | Linear pCT107 vector in which polyA linked to dhfr, has been made inoperable by treatment with Cla I |

The transfection was carried out in the following manner. CHO DG44 cells were seeded into 6-well plates at a density of $0.5 \times 10^6$ cells/well using MEMα medium (1140076, Invitrogen) supplemented with 10% FBS (12105, Sigma), and after 24 hours, the medium was replaced with MEMα medium without FBS. After 30 minutes, 2.5 µg of the vector DNA of each of the control group (A), the test group (B), the test group (C) and the test group (D) together with 500 µl of Opti-SFM medium (12309-050, Invitrogen) was added to each well, after which 6.25 µl of LTX (15338-100, Invitrogen) was added thereto and vortexed well using a vortex mixer. The resulting mixture was allowed to stand at room temperature for 30 minutes, and then 500 µl of the mixture was added to each well. After 4 hours, the medium was replaced with serum-containing MEMα medium.

Example 3

Confirmation of Expression of IgG Antibody Gene Using ELISA

In order to confirm whether the IgG antibody gene was expressed, ELISA was carried out 3 days after the transfection. First, goat anti-human immunoglobulin G (Fcγ) (109-006-098, Jackson ImmunoReserarch) was adsorbed onto 96-well microtiter plates (449824, Nunc). The plates were blocked with phosphate-buffered saline (PBS) containing 1% BSA (Bovine Serum Albumin), and then a serially diluted sample was added to each well. After the plates have been allowed to stand at room temperature for 2 hours, the sample was treated with peroxidase-labeled goat anti-human K antibody (11514, Sigma) for detection. After standing at room temperature for 1 hour, the sample was allowed to react with tetramethyl benzidine (TMB), and 1 N HCl was added thereto to stop the reaction. As a standard, human IgG1 kappa purified from myeloma plasma (A7164, Sigma) was used from a concentration of 250 ng/μl. The absorbance at 450/650 nm was measured using a plate reader (Spectramax plus 384, Molecular Device).

Figure 2:
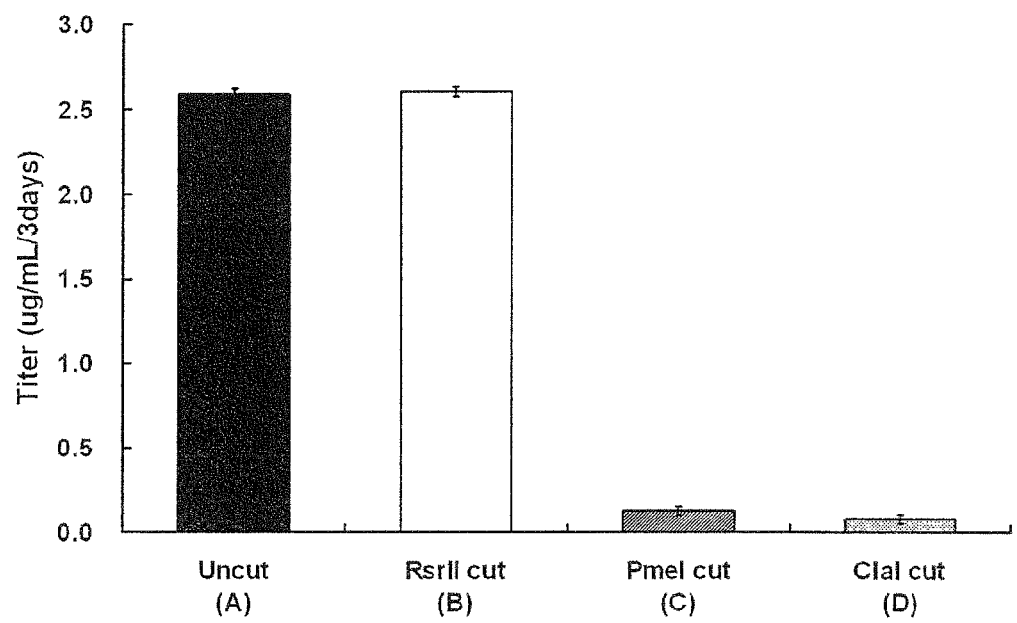
FIG. 2 shows the results of measuring the expression titers of IgG antibody in CHO cells transfected with each of expression vectors of a control group (A), a test group (B), a test group (C) and a test group (D).

As can be seen in FIG. 2, IgG was normally expressed in the control group (A) and the test group (B), but was not normally expressed in the test group (C) and the test group (D). This suggests that, in the case of the gene expression cassette in which the polyA linked to the 3' end of the corresponding gene has been made inoperable, the protein that is encoded by the corresponding gene is not normally expressed (test group (C) and test group (D)).

Also, it has been found that, in transient transfection in which cells were cultured at least in the absence of a selective drug, the expression of a protein (DHFR protein) encoded by the selectable marker gene did not influence the expression level of a protein (particularly antibody) encoded by the corresponding gene in the expression vector.

Example 4

Selection of Cell Clones Using dhfr Marker Gene on which polyA does not Operate

In order to manipulate a polyA linked to the 3' end of the selectable marker gene dhfr such that it does not operate, a pCT107 vector was treated with a Rsr II restriction enzyme (R0501, NEB) under the same conditions as those described in Example 1, thereby obtaining a test group (E). The resulting vector was transfected into a CHO DG44 cell line. As a control group, a pCT107 vector not treated with a restriction enzyme (control group (A)) was used. The transfection was carried out in the same manner as Example 1. The expression levels of IgG antibody measured 3 days after the vector of the control group (A) and the vector of the test group (E) were introduced into the cell line were 3.9 μg/μl and 3.8 μg/μl, respectively. 3 days after the start of culture following the transfection, the cells of each of the control group (A) and the test group (E) were transferred onto 96-well plates, and then cultured in SFM4CHO™ medium (SH30549.02, HyClone) containing 2% FBS (fetal bovine serum) and 100 nM MTX (813630, Bedford Labs). In the case of the control group (A), 0.5×10$^6$ cells/96-well plate were seeded and cultured, and in the case of the test group (E), 2×10$^6$ cells/96-well plate were seeded and cultured.

Figure 3:
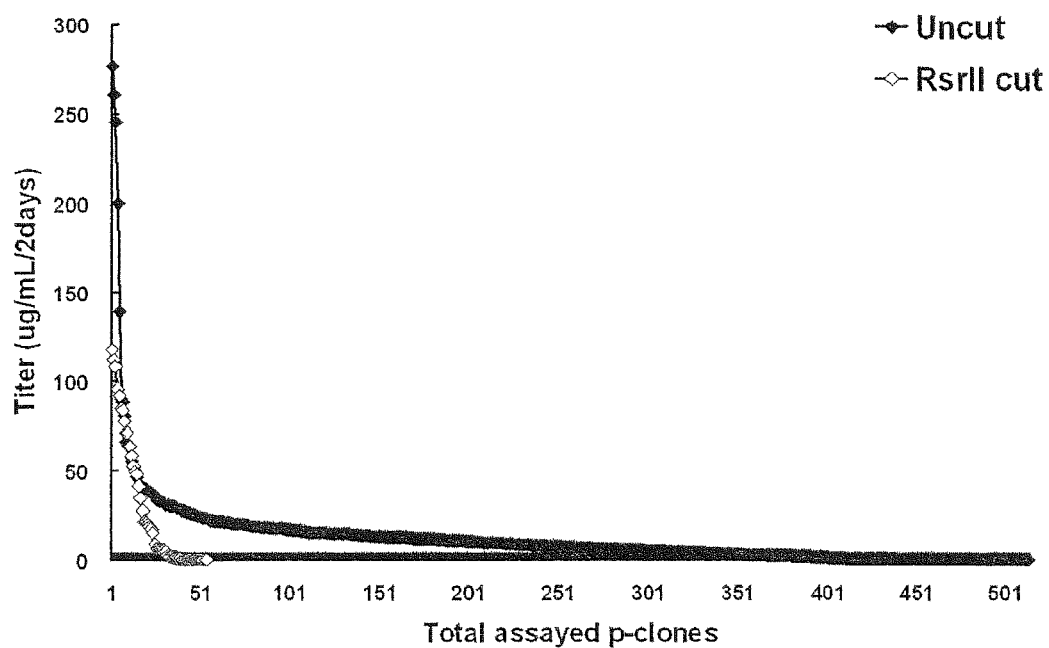
FIG. 3 is a graph showing a comparison of titers shown in the processes in which cell clones were selected depending on the presence or absence of a polyA linked to dhfr gene at the 96-well plate scale.
Figure 4:
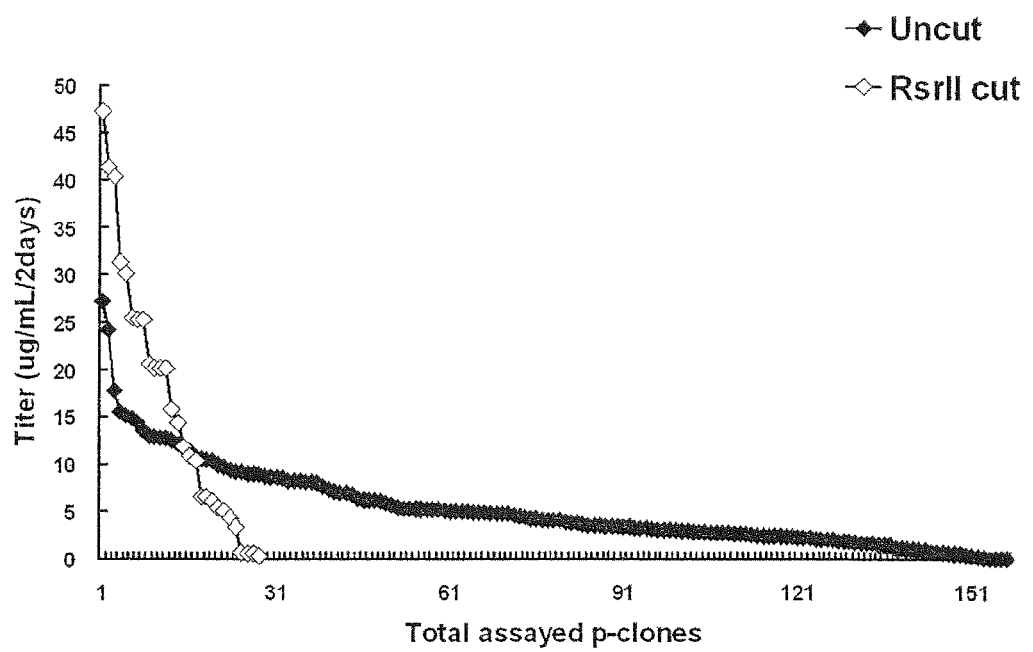
FIG. 4 is a graph showing a comparison of titers shown in the processes in which cell clones were selected depending on the presence or absence of a polyA linked to dhfr gene at the 24-well plate scale.
Figure 5:
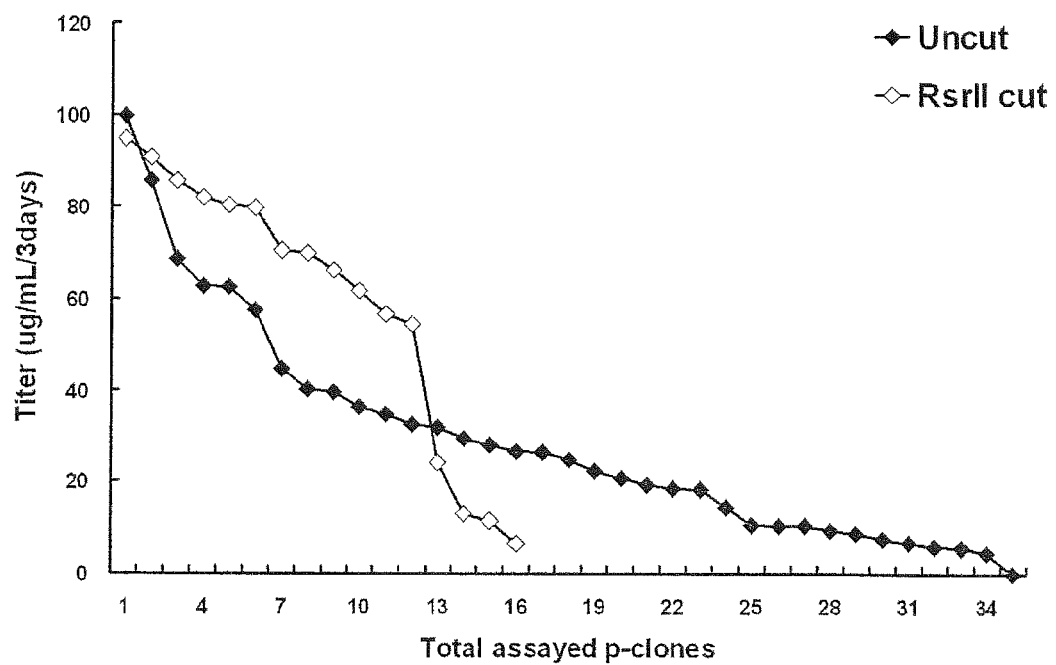
FIG. 5 is a graph showing a comparison of titers shown in the processes in which cell clones were selected depending on the presence or absence of a polyA linked to dhfr gene at the 6-well plate scale.

After the culture, the number of wells in which growing cells existed was examined. As a result, in the case of the control group (A), 514 wells (19.8%) among a total of 2,592 wells showed cell growth, and in the case of the test group (E), 54 wells (2.5%) among a total of 2112 wells showed cells growth. In other words, growing cells existed in 19 wells per 96-well plate in the control group (A), and growing cells existed in 2.5 wells per 96-well plate in the case of the test group. Based on the results, when assuming that cells growing in each well with positive cell growth were derived from a single cell, the ratio of growing cells between the groups was 31:1 (control group (A): test group (E)), which was a greater difference (Table 2 and FIGS. 3 to 5).

TABLE 2

|  | Control group (A) | Test group (E) | Control group (A)/ Test group (E) |
|---|---|---|---|
| Number of seeded plates | 27 | 22 | — |
| Total number of wells | 2,592 | 2,112 | — |
| Number of wells showing positive growth reaction | 514 (19.8%) | 54 (2.5%) | 9.5 |
| Number of wells showing positive growth reaction/ number of seeded plates | 19.8 | 2.6 | 7.8 |
| Seeding density (cells/plate) | 0.5 × 10$^6$ | 2.0 × 10$^6$ | — |
| Total number of seeded cells | 1.35 × 10$^7$ | 4.4 × 10$^7$ | — |
| Ratio of positively growing cells | 1/26,264 | 1/814,815 | 31 |

Then, among wells having growing cells, wells showing high titers were selected. As a result, in the case of the control group (A), 157 wells were selected from among 514 wells, and in the case of the test group (E), 28 wells were selected from among 54 wells. Then, the cells in the selected wells were transferred to and cultured in 24-well plates while increasing the culture scale, and after 3 days, six cell populations showing high titers in the 24-well plates were selected from each of the control group (A) and the test group (E) and seeded and cultured in 6-well plates. The six cell populations selected from each of the control group (A) and the test group (E) were named "p-clones", and they were seeded and cultured in Erlenmeyer flasks using a FBS- and MTX-free medium under stirring. The productivities of the control group (A) and the test group (E) were compared with each other.

As a result, in the case of the control group (A), only one p-clone among the six p-clones showed a productivity of about 100 μg/μl/3 days, whereas in the case of the test group (E), four p-clones among the six p-clones showed a productivity of about 100 μg/μl/3 days (FIG. 6).

Example 5

Cell Growth Conditions for Utility of Selectable Marker Genes

In order to examine the utility of general selectable markers which are not involved in gene amplification in various cell lines, a drug acting on each selectable marker gene was applied to each cell line under the conditions shown in Table 3, and the inhibition of cell growth was measured.

The cell lines used in the experiment were CHO K1 and F2N78 (human cell line), and each of the cell lines, cultured in CD Opti CHO medium (12681, Invitrogen) and EX-CELL 293 serum-free medium (14571c, Sigma), was cultured in the same medium in this Example. 5 W of each of the cell lines was added to each well of 6-well plates at densities of 5)($10^4$ cells/W and $15 \times 10^4$ cells/W, which corresponded to densities of $1 \times 10^6$ cells/96-well plate (20 ml) and $3 \times 10^6$ cells/96-well plate (20 ml), respectively. The densities of $1 \times 10^6$ cells/96-well plate and $3 \times 10^6$ cells/96-well plate were cell densities used in the selection method of Example 6 using the polyA-deleted selectable marker. Three drug concentrations were used for each cell line, and half of the medium (2.5 W) in each well was removed every three days and replaced with the same amount of fresh medium. The types and details of drugs used in this experiment are shown in Table 4 below. Herein, the fresh medium always contained a specified concentration of a drug.

After 2 weeks, through cell staining with trypan blue, it was found that no growth of untransfected CHO K1 cells and F2N cells was observed in all the drug treatment conditions (Table 3). Namely, the presence of growing cells in cultures under the drug treatment following transfection indicates that the treated drugs are inactivated by the transfected selectable marker genes, whereby the cells grow.

TABLE 3

Various drug treatment conditions for CHO K1 cells and F2N cells

|  | Blasticidin (μg/ml) | G418 (μg/ml) | Hyg B (μg/ml) | puromycin (μg/ml) | Zeocin (μg/ml) |
|---|---|---|---|---|---|
| Abbreviation of selectable marker gene | Bsd | neo | Hyg | Pag | Zeo |
| CHO K1 | 10 | 400 | 250 | 4 | 250 |
|  | 20 | 800 | 500 | 8 | 500 |
|  | 40 | 1200 | 1000 | 16 | 1000 |
| F2N | 10 | Not applicable* | 200 | 2 | 200 |
|  | 20 |  | 400 | 4 | 400 |
|  | 40 |  | 800 | 8 | 800 |

(*F2N cells contained neo gene)

TABLE 4

Information on selective drugs

| Selective drug | Manufacturer | Selectable marker gene | Cat# |
|---|---|---|---|
| G418 or Geneticin®  (Invitrogen brand name) | Invitrogen | G418 | 10131-035 |
| Puromycin | Invitrogen | pac | A11138-03 |
| BlasticidinS HCl | Invitrogen | bsd, bsr | A11139-03 |
| Zeocin ™ | Invitrogen | sh ble(zeo$^r$) | R250-01 |
| Hygromycin B (mycophenolic acid) | Invitrogen | hyg, hph | 10678-010 |

Example 6

Establishment of Protein-Producing Cell Line Using Pac Selectable Marker Gene without polyA As confirmed above, the selection method using the dhfr selectable marker gene to which a polyA has been inoperably linked is very efficient in terms of reduction of the cost and time for selecting high producer clones in the CHO DG44 cell line. In order to examine whether this selection method is also applied to selectable markers other than the dhfr gene and cell lines other than the CHO DG44 cell line, in this Example, a selection method using a pac selectable marker gene from which a polyA has been completely deleted was applied to the CHO K1 cell line to examine its efficacy.

In order to completely remove the function of the polyA, in this Example, a pCT130 vector and a pCT129 vector were constructed by completely removing a dhfr transcription unit (promoter-dhfr gene-polyA) from an immunoglobulin expression vector (pCT112 vector) and inserting promoter-pac gene or promoter-pac gene-polyA therein (FIGS. 7 and 8). The vectors were constructed in the following manner. A SV40 promoter and a pac gene-coding sequence were isolated from a pac gene-containing pPUR vector (631601, Clontech) by using Pvu II (10-642-690-0014, Roche) and Xba I (R0145S, NEB) restriction enzymes and cloned into a pCT112 vector from which the dhfr transcription unit had been removed by using Nru I (R0192L, NEB) and Xba I restriction enzymes, thereby constructing a pCT130 vector (FIG. 7). Also, for comparison therewith, a SV40 promoter, pac gene and polyA were isolated from a pPRU vector by using Pvu II and BamH I (R0136S, NEB) restriction enzymes and cloned into a pCT112 vector from which the dhfr transcription unit has been removed, thereby constructing a pCT129 vector (FIG. 8).

The CHO K1 cell line was transfected with each of the pCT129 vector and the pCT130 vector, and after 2 days, the cells were seeded into 96-well plates using medium supplemented with various concentrations of puromycin as shown in Table 5 below. The medium used in this Example was CD OptiCHO medium containing no FBS. In the control group transfected with the pCT129 vector, a seeding density of $0.3 \times 10^6$ cells/plate and a selective condition of 6 μg/μl puromycin were proper, and in the test group transfected with the pCT130 vector, a seeding density of $3 \times 10^6$ cells/plate and a selective condition of 6 μg/μl puromycin were proper. Particularly, in this Example, similar numbers of p-clones were selected from the control group containing the selectable marker with polyA and the test group containing the selectable marker without polyA by performing several rounds of transfection experiments, and the expression levels of immunoglobulin in the p-clones were compared with each other.

TABLE 5

Comparison of selective conditions of cells seeded into 96-well plates

| pCT129 vector (control group: use of pac gene with polyA) | | pCT130 vector (test group: use of pac gene without polyA) | |
|---|---|---|---|
| Seeding density ($\times 10^6$ cells/plate) | Puromycin (μg/ml) | Seeding density ($\times 10^6$ cells/plate) | Puromycin (μg/ml) |
| 0.1 | 6 | 1 | 10 |
|  | 8 | 3 | 6 |
| 0.3 | 6 |  | 8 |
|  |  |  | 10 |

The antibody productions of wells with cells growing under the selective conditions of Table 5 above were measured by ELISA and p-clones showing high antibody productivity were selected from the 96-well plates (FIG. 9) and transferred into 24-well plates. Then, in order to measure antibody productivity again, each clone sample was subjected to a 2-fold serial dilution and assayed by ELISA (FIG. 10). Among the p-clones, 41 p-clones showing high antibody productivity were transferred into 6-well plates, and then the antibody productivities thereof were measured (FIG. 11). As can be seen in FIGS. 9 to 11, in the two processes for selecting p-clones having high antibody productivity (selection processes in 96-well plates and 24-well plates), more p-clones having high productivity were selected from those derived from the pCT130 vector (test group) containing no polyA than those derived from the pCT129 vector (control group) containing polyA.

Also, p-clones 129-4 and 130-35 having high productivity were selected from each group and subjected to limiting dilution cloning (LDC). The selected p-clones were treated with 2 μg/μl puromycin when they were cultured in 96-well plates, whereas no puromycin was added when the clones were cultured in 24-well plates and 6-well plates. By conducting the selection processes at the 96-well plate, 24-well plate and 6-well plate scales, five single cell clones having high productivity were selected from each group, and the productivity in 6-well plates (FIG. 12) and the productivity in shake flasks (FIG. 13) were examined. The productivity in shake flasks was measured in duplicate by conducting batch culture under the same conditions.

As can be seen in FIG. 12, the productivity of the clones derived from the pCT130 vector (25-32 μg/μl/3 days) was about 2 times higher than that of the clones derived from the pCT129 vector (7-18 μg/μl/3 days). This suggests that clones having higher productivity can be constructed from a vector containing no polyA in the selectable marker. In the shake-flask batch culture conditions allowing productivity to be examined in more substantial terms, as shown in FIG. 13, the clones derived from the pCT130 vector (test group) containing no polyA in the selectable marker showed a productivity of 62-72 μg/μl, whereas the clones derived from the pCT129 vector (control group) containing polyA in the selectable marker showed a productivity of 2-10 μg/μl. In these cell growth conditions, the cell growth rates were similar between the two groups, but the clones derived from the pCT130 vector (test group) showed a productivity six times higher than that of the clones derived from the pCT129 (control group). This remarkable difference might be attributable to the phenomenon in which, in the case of the clones derived from the pCT129 vector (control group), the expression of IgG was readily inhibited or IgG gene was readily deleted in the absence of selective conditions.

The above results show that transfecting a cell line with the expression vector containing the selectable marker without polyA according to an embodiment of the present invention, rather than the expression vector containing the selectable marker with polyA, is a method of obtaining a cell line having a high antibody expression level. Accordingly, the selection method according to an embodiment of the present invention can reduce the time for selecting high-productivity cell clones, compared to a conventional stepwise gene amplification strategy which comprises carrying out multiple amplification steps while increasing the amount of MTX. Thus, the labor and cost for developing cell clones having high productivity can be reduced.

The invention claimed is:

1. A method of selecting recombinant cells, comprising the steps of:
  (i) transfecting an isolated population of CHO cells with an expression vector comprising:
    (a) a first gene expression cassette comprising a selectable marker gene from which a polyadenylation signal (polyA) has been removed, wherein the selectable marker gene is the dihydrofolate reductase (dhfr) gene or the puromyocin-N-acetyltransferase (pac) gene; and
    (b) a second gene expression cassette which encodes a recombinant protein of interest and to which a polyA has been operably linked,
  (ii) culturing the transfected population of CHO cells under selective conditions comprising 100 nM methotrexate when the selectable marker gene is dhfr or 6-10 μg/mL puromyocin when the selectable marker gene is the pac gene; and
  (iii) selecting recombinant CHO cells which have survived the selective conditions, wherein the selected recombinant CHO cells express the protein of interest at least six times higher as compared to a recombinant CHO cell having an expression vector in which the selectable marker gene has an operably linked poly A.

2. The method of claim 1, wherein the recombinant protein of interest is a monoclonal antibody.

* * * * *